United States Patent
Ishikawa et al.

(10) Patent No.: US 9,468,621 B2
(45) Date of Patent: Oct. 18, 2016

(54) METAL-SALEN COMPLEX COMPOUND RESPONSIVE DRUG AND INTRA-CORPOREAL BEHAVIOR CONTROL SYSTEM FOR METAL-SALEN COMPLEX COMPOUND

(71) Applicants: IHI Corporation, Tokyo (JP); Yoshihiro Ishikawa, Tokyo (JP)

(72) Inventors: Yoshihiro Ishikawa, Tokyo (JP); Haruki Eguchi, Tokyo (JP)

(73) Assignees: IHI Corporation, Tokyo (JP); Yoshihiro Ishikawa, Tokyo (JP)

( * ) Notice: Subject to any disclaimer, the term of this patent is extended or adjusted under 35 U.S.C. 154(b) by 0 days.

(21) Appl. No.: 14/349,112

(22) PCT Filed: Sep. 19, 2012

(86) PCT No.: PCT/JP2012/073900
§ 371 (c)(1),
(2) Date: Apr. 2, 2014

(87) PCT Pub. No.: WO2013/051389
PCT Pub. Date: Apr. 11, 2013

(65) Prior Publication Data
US 2014/0235684 A1    Aug. 21, 2014

(30) Foreign Application Priority Data

Oct. 4, 2011  (JP) ................. 2011-220449

(51) Int. Cl.
| | |
|---|---|
| *A61K 31/295* | (2006.01) |
| *A61K 31/16* | (2006.01) |
| *A61K 31/375* | (2006.01) |
| *A61K 31/4196* | (2006.01) |
| *A61K 31/21* | (2006.01) |
| *A61K 41/00* | (2006.01) |

(52) U.S. Cl.
CPC ............ *A61K 31/295* (2013.01); *A61K 31/16* (2013.01); *A61K 31/21* (2013.01); *A61K 31/375* (2013.01); *A61K 31/4196* (2013.01); *A61K 41/00* (2013.01)

(58) Field of Classification Search
CPC .................................................. A61K 31/295
See application file for complete search history.

(56) References Cited

U.S. PATENT DOCUMENTS

| 5,403,834 A | 4/1995 | Malfroy-Camine et al. |
| 5,549,915 A | 8/1996 | Volkonsky et al. |
| 2011/0214840 A1 | 9/2011 | Sakamoto et al. |

FOREIGN PATENT DOCUMENTS

| CN | 102239138 A | 11/2011 | |
| EP | 23 57166 A1 | 8/2011 | |
| EP | 2357166 A1 * | 8/2011 | ........... A61K 31/135 |
| JP | 2001-10978 A | 1/2001 | |
| JP | 2009-220007 A | 10/2009 | |
| RU | 2157213 C2 | 10/2000 | |
| WO | 9413300 A1 | 6/1994 | |
| WO | 2010/058280 A1 | 5/2010 | |
| WO | 2010-058520 A1 | 5/2010 | |
| WO | WO 2010058280 A1 * | 5/2010 | ........... A61K 31/135 |

OTHER PUBLICATIONS

Baudry et al. "Salen-Manganese Complexes Are Superoxide Dismutase-Mimics" Biochemical and Biophysical Research Communications, 1993, vol. 192, pp. 964-968.*
Yang et al. "Deferasirox : a review of its use in the management of transfusional chronic iron overload" Drugs, 2007, vol. 67, pp. 2211-2230.*
Kurebe et al. "General Toxicity and Immunotoxicity of Antitumor Agents" The Journal of Toxicological Sciences, 1991, vol. 16, Supplement II, pp. 21-25.*
International Search Report from corresponding International Application No. PCT/JP2012/073900 mailed Oct. 16, 2012.
International Publication from corresponding International Application No. PCT/JP2012/073900 published on Apr. 11, 2013.
Baudray, M. et al, Salen-manganese complexes are superoxide dismutase-mimics, Biochemical and Biophysical Research Communications, 1993, vol. 192, No. 2, p. 964-8.
Kurebe, Masaru et al, General Toxicity and Immunotoxicity of Antitumor Agents, Journal of Supplement II, p. 21-25.
Hiizu Iwamura "Design of Organic Ferromagnets" Feb. 1989, pp. 76-88 (cited in the original specification) (non-patent literature).
Kristy Cochran et al. "cis-Diamminodichloronickel and Its Interaction With Guanine and Guanine-Cytosine Base Pair" vol. 13, No. 2, Apr. 2002, pp. 133-140 (cited in the original specification) (non-patent literature).
V.P. Choudhry, et al "Current Status of Iron Overload and Chelation with Deferasirox", Department of Hematology, All India Institute of Medical Sciences, New Delhi, Indian Journal of Pediatrics, Aug. 2007, vol. 74, pp. 759-764.
M. Miller, et al "Syntheses and Therapeutic Potential of Hydroxamic Acid Based Siderophores and Analogues", Chemical Reviews, 1989, vol. 89, pp. 1563-1579.
Russian Office Action dated Sep. 29, 2015.

* cited by examiner

*Primary Examiner* — Joseph Kosack
(74) *Attorney, Agent, or Firm* — Brundidge & Stanger, P.C.

(57) ABSTRACT

A metal-salen complex compound responsive drug, which has an antidotal property capable of neutralizing cytotoxicity of a metal-salen complex compound, and an intra-corporeal behavior control system for the metal-salen complex compound are provided. This metal-salen complex compound responsive drug contains an effective amount of a metal chelating agent to suppress side effects by the metal-salen complex compound.

5 Claims, 2 Drawing Sheets

METAL-SALEN COMPLEX COMPOUND RESPONSIVE DRUG AND INTRA-CORPOREAL BEHAVIOR CONTROL SYSTEM FOR METAL-SALEN COMPLEX COMPOUND

TECHNICAL FIELD

The present invention relates to a metal-salen complex compound responsive drug for neutralizing cytotoxicity of a metal-salen complex compound and an intra-corporeal behavior control system for the metal-salen complex compound.

BACKGROUND ART

Generally, a drug is administered into a living body and reaches its affected site, and induces a therapeutic effect by locally exhibiting its pharmacological effect at the affected site; however, even if the drug reaches tissues (that is, normal tissues) other than the affected site, the drug will not contribute to any medical treatment.

Accordingly, what is important is how to efficiently deliver the drug to the affected site. The technique of guiding the drug to the affected site is called drug delivery, and this is a field in which researches and development have been actively conducted in recent years. This drug delivery has at least two advantages. One advantage is that a sufficiently high drug concentration can be obtained in the affected site tissues. Specifically speaking, pharmacological effects will not be obtained unless the drug concentration at the affected site is of a certain level or higher; and the therapeutic effects cannot be expected with a low concentration. However, a sufficiently high drug concentration can be obtained at the affected site tissues by guiding the drug to the affected site.

The second advantage is that side effects to the normal tissues can be suppressed and a drug dosage can be limited to the minimum necessary by guiding the drug to only the affected site tissues.

Such drug delivery is most effective in cancer treatment using anticancer agents. Since most anticancer agents inhibit the cell growth of cancer cells which divide actively, they also inhibit the cell growth of tissues, whose cells divide actively, in normal tissues such as bone marrow, hair roots, digestive tract linings and the like. Thus, a cancer patient to whom an anticancer agent is administered become subject to side effects such as anemia, hair loss, and vomiting.

Since these side effects impose a heavy burden on the patient, it is necessary to limit the dosage. So, the problem is that the pharmacological effects of the anticancer agent cannot be sufficiently obtained. In a worst case scenario, there is a possibility that the side effects may kill the patient.

Thus, it is expected that cancer treatment can be performed effectively while suppressing the side effects by guiding the anticancer agent to the cancel cells by means of drug delivery and making the anticancer agent exhibit the pharmacological effects on the cancer cells in a concentrated matter.

Local anesthetics have similar problems. A local anesthetic is used to treat hemorrhoidal disease, stomatitis, periodontal disease, dental caries, tooth extraction, and local itching or pain of mucous membranes or skin due to surgeries or the like. Lidocaine (product name: Xylocaine) is known as a representative local anesthetic. Although Lidocaine is superior in terms of instantaneous effect, it also has an anti-arrhythmic effect if it spreads systemically; and, therefore, Lidocaine affects a heart significantly.

Moreover, upon performing spinal anesthesia, if Lidocaine is injected as an anesthetic into a spinal fluid, it spreads within the spinal fluid; and there is a possibility that it might cause critical side effects by reaching spinal cords in a cervical region and causing damage to a respiratory function.

As a specific method of the drug delivery, for example, there is a method of using a carrier. This method is to have a carrier which can be easily concentrated at the affected site carry the drug and deliver it to the affected site.

A magnetic substance is considered highly probable as the carrier and there is a proposed method of attaching a carrier, which is a magnetic substance, to the drug and accumulating the drug at the affected site by means of a magnetic field (for example, see Patent Literature 1).

However, it has been found that when the magnetic substance is used as the carrier, oral administration is difficult, carrier molecules are generally enormous, and there are technical problems in binding intensity and affinity between the carrier and drug molecules. So, the practical use of the magnetic substance was difficult in the first place.

Therefore, the inventor of the present invention suggested a metal-salen complex compound as an organic magnetic compound that is anticarcinogenic by itself and is capable of binding with functional molecules such as other medical molecules, enzymes, and proteins (for example, see Patent Literature 2). In this case, the metal-salen complex compound administered to an individual can be guided to a target tissue by a magnetic field applied to the individual. Therefore, it is possible to proceed with a drug treatment, while localizing the effects of the metal-salen complex compound at a target affected site tissue and reducing its side effects.

Moreover, a review article about an organic magnetic substance is introduced, which describes that a magnet is produced with polymeric materials by means of synthesis of "high-spin molecules" having more parallel spins than those of conventional metallic magnetic substances (for example, see Non Patent Literature 1).

Furthermore, a technique that replaces platinum contained in cisplatin with another element is also introduced (for example, see Non Patent Literature 2).

CITATION LIST

Patent Literature

[Patent Literature 1] Japanese Patent Application Laid-Open (Kokai) Publication No. 2001-10978
[Patent Literature 2] International Publication WO2010/058280
[Non Patent Literature 1] Hiizu Iwamura, "Molecular Design Aimed at Organic Ferromagnetic Substances," February 1989 issue, p.p. 76-88
[Non Patent Literature 2] Krsity Cochran et al., Structural Chemistry, 13 (2002), p.p. 133-140

SUMMARY OF INVENTION

Problems to be Solved by the Invention

However, Non Patent Literature 1 or Non Patent Literature 2 does not refer to magnetization of the drug itself.

Furthermore, a treatment by an anti-tumor agent is performed by repeating a cycle of a combination of an administration period and an off period more than once. If the application of an external magnetic field to the individual is stopped during the rest period, the metal-salen complex compound will be released from the affected site tissue and spread systemically at once due to blood circulations and there is a possibility that the side effects might occur suddenly due to elevation in circulating levels. However, there is no antidote for the sudden side effects by the metal-salen complex compound.

The present invention was devised in light of the above-described circumstances and it is an object of the invention to provide a metal-salen complex compound responsive drug, which has an antidotal property capable of neutralizing cytotoxicity of a metal-salen complex compound, and an intra-corporeal behavior control system for the metal-salen complex compound.

Solution to Problem

As a result of thorough examination in order to achieve the above-described object, the inventor of the present invention has found that the metal-salen complex compound is inactivated by having metal of the metal-salen complex compound bound through a coordinate bond by a metal chelating agent; and even when application of a magnetic field to an affected site tissue is stopped and the metal-salen complex compound circulates systemically, the cytotoxicity effect of the metal-salen complex compound can be suppressed by administering the metal chelating agent.

Therefore, in order to achieve the above-described object, the present invention provides a metal-salen complex compound responsive drug that is an antidote containing an effective amount of a metal chelating agent to suppress side effects of the metal-salen complex compound.

Moreover, the metal-salen complex compound responsive drug according to the present invention may be an antidote that is a combination of the metal-salen complex compound, which is administered to a human or an animal and then guided to an affected site tissue by a magnetic field applied to the affected site tissue, and an effective amount of the metal chelating agent to suppress side effects of the metal-salen complex compound, which may be caused when the metal-salen complex compound is released from the magnetic field.

An effective ratio of the metal chelating agent for neutralizing cytotoxicity of the metal-salen complex compound is 0.3 μM or more and 50 μM or less or more preferably 7.5 μM or more and 30 μM or less. If the ratio of the metal chelating agent is 0.3 μM, it is difficult to effectively neutralize the cytotoxicity of the metal-salen complex compound; and if the ratio of the metal chelating agent is 50 μM or more, the concentration of the chelating agent becomes excessive and the metal chelating agent becomes no longer effective.

Furthermore, the present invention provides a metal-containing anti-tumor agent responsive drug that contains an effective amount of a metal chelating agent to suppress side effects of an anti-tumor agent containing metal.

Furthermore, the present invention provides an intra-corporeal behavior control system for a metal-salen complex compound, including: a step of administering a metal-salen complex compound to a human or an animal; a step of externally applying a magnetic field to an affected site tissue and guiding the metal compound to the magnetic-field-applied area; a step of administering an effective amount of a metal chelating agent to suppress side effects of the metal-salen complex compound, which are caused by release of the metal-salen complex compound from the affected site tissue and systemic circulation of the metal-salen complex compound due to cessation or termination of the application of the magnetic field.

Advantageous Effects of Invention

According to the present invention, it is possible to provide a metal-salen complex compound responsive drug, which has an antidotal property capable of neutralizing cytotoxicity of a metal-salen complex compound, and an intra-corporeal behavior control system for the metal-salen complex compound.

DESCRIPTION OF EMBODIMENTS

Figure 1:
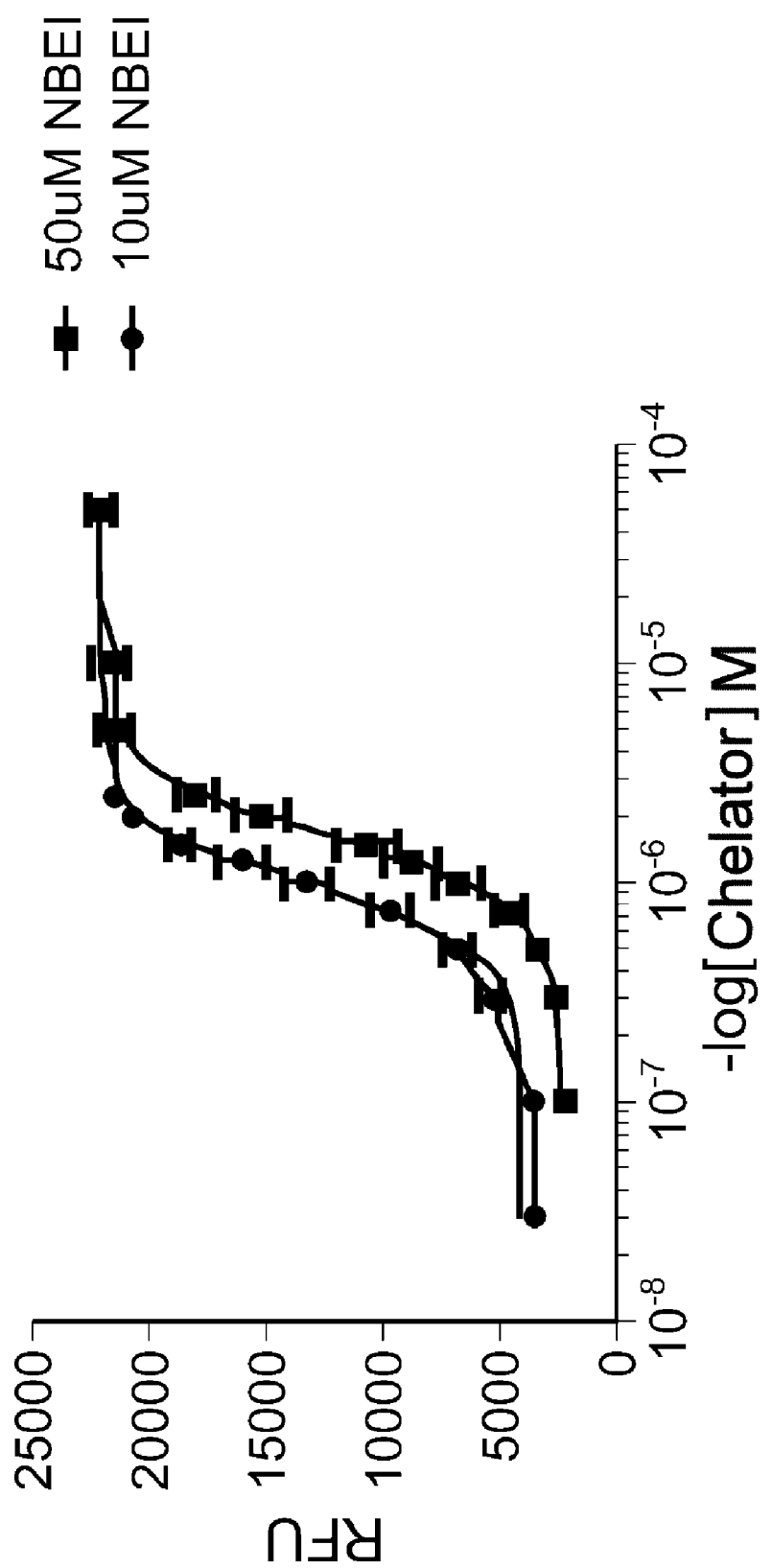
FIG. 1 is a graph showing measurement results of Example 1 (administration of deferoxamine [first metal chelating agent]) of the present invention.

For example, a known oral iron chelating agent which is indicated below (I) and is a therapeutic drug for a chronic iron overload disorder associated with blood transfusion can be used.

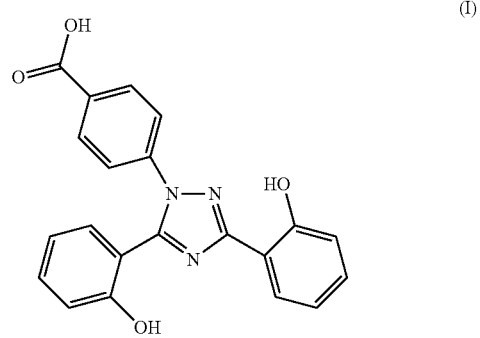 [SMILES: O=C(O)c1ccc(-n2nc(-c3ccccc3O)nc2-c2ccccc2O)cc1]

(I)

General Name: deferasirox
Chemical Name: 4-[3,5-Bis(2-hydroxyphenyl)-1,2,4-triazol-1-yl]benzoic acid
Molecular Formula: $C_{21}H_{15}N_3O_4$
Molecular Weight: 373.36
CAS Registration Number: 201530-41-8

Furthermore, as another metal chelating compound, it is possible to use, for example, a compound which is indicated below as (II), is one of chelating agents used to remove excessive iron from the body, is known as a therapeutic drug for iron overload disorder and iron intoxication, and is administered via intramuscular injection and intravenous drip injection.

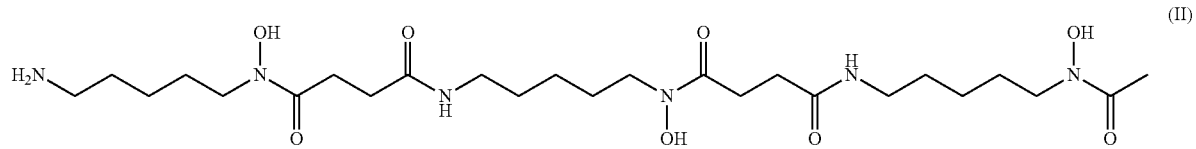 [SMILES: CC(=O)N(O)CCCCCNC(=O)CCC(=O)N(O)CCCCCNC(=O)CCC(=O)N(O)CCCCCN]

(II)

General Name: deferoxamine
Chemical Name: (N-(5-aminopentyl)-N-hydroxy-N'-[5-(N-hydroxy-3-{[5-(N-hydroxyacetamido) pentyl]carbamoyl}propanamido) pentyl]butanediamide)
Molecular Formula: $C_{25}H_{48}N_6O_8$
Molecular Weight: 560.684
CAS Registration Number: 70-51-9

Usage and dosages of these chelating agents may be subject to known usage and dosages. However, the dosage of the metal chelating agent may be increased or decreased depending on a concentration of the metal-salen complex compound administered to an individual. An effective ratio of the metal chelating agent to neutralize the cytotoxicity of the metal-salen complex compound is 0.3 µM or more and 50 µM or less or more preferably 7.5 µM or more and 30 µM or less. These chelating agents are effective in eliminating iron that has been excessively ingested as the metal-salen complex compound. It is more effective to add known vitamin C, which has an antidotal effect against side effects of anti-tumor agents, to the drug according to the present invention.

The metal-salen complex compound which is a target to be detoxified by the metal chelating agent has a quadridentate ligand (N, N, O, O) for metal and is an organic metal compound (III) having, for example, salen (N,N'-bis(2-hydroxybenzylidene) ethylene diamine (systematic name) N,N'-bis(salicyliden) ethylene diamine) as a ligand. There is no particular limitation regarding the metal (M) as long as it can constitute a salen complex; and the metal (M) may be, for example, iron, cobalt, nickel, manganese, chromium, molybdenum, platinum, iridium, ruthenium, or palladium. The metal-salen complex compound is disclosed in International Publication WO2008/001851 and International Publication WO2010/058280.

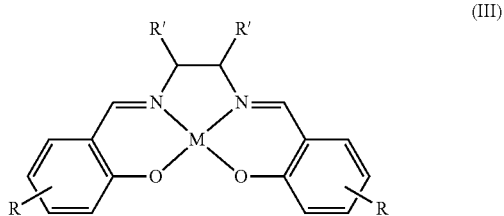

(III)

EXAMPLES

Example 1

Method for Detoxifying a Divalent-Iron-Salen Complex Compound, Using Deferoxamine (Principle)

If calcein (Calcein: fluorescent indicator) is used solely, it emits light (an RFU value increases); however, if calcein binds with a ferrous-salen complex compound, light emission diminishes (the RFU value decreases). Accordingly, if deferoxamine (deferoximine: the above-mentioned structural formula (II)) exists, iron ions of the ferrous-salen complex compound are adsorbed by the deferoxamine and ferrous-salen ligands are detached from calcein. As a result, the amount of the calcein-divalent-iron-salen complex compound decreases and the light emission diminishes. You can tell that as an amount of emitted light decreases, the metal-salen complex compound combines with the metal chelating agent.

(Method)

The ferrous-salen complex compound (M=Fe, R=R'=H) indicated as the aforementioned structural formula (III) was produced based on descriptions of WO 2010/058280. Next, the 10 µM ferrous-salen complex compound and 10 µM Calcein AM (trade name; made by SIGMA Corporation) were mixed and the mixture was let stand for one hour, and then absorbance was measured and it was confirmed that sufficient light was emitted. Subsequently, 15 µM deferoxamine was administered to this ferrous-salen complex compound—calcein AM complex—and measurement was performed one hour later by using a measuring device (parkinermar ARVO) (λexc=485 nm, λem=520 nm). FIG. 1 shows the results.

(Results)

Referring to FIG. 1, it was confirmed that when the ferrous-salen complex compound was added to Calcein AM, the RFU (Relative Fluorescent Unit) value was low. However, it was also confirmed that when the chelator (deferoxamine) continued to be added, the RFU value increased. Furthermore, when the concentration of the ferrous-salen complex compound (NBEI) was high as illustrated in FIG. 1, this curve shifted to the right. In other words, a larger amount of the chelator is required to keep the same RFU value. This means that if the concentration of the ferrous-salen complex compound is high, a large amount of the chelator is required to neutralize it. Referring to FIG. 1, a unit for [Chelator] is a volume molar concentration [mol/L] which is a concentration unit. When the ferrous-salen complex compound (NBEI) was 50 µM, EC50 (50% effective concentration of a maximum reaction value) was 1.627e-006; and when the ferrous-salen complex compound (NBEI) was 10 µM, EC50 was 9.661e-007.

Method for Detoxifying Ferrous-Salen Complex Compound, Using Deferoxamine and Vitamin C A 15 µM of deferoxamine and vitamin C was administered to the ferrous-salen complex compound—calcein AM complex—which was produced in Example 1 above and measurement was performed one hour later by using the measuring device (parkinermar ARVO) (λexc=485 nm, λem=520 nm). As a result, it was also confirmed that when the ferrous-salen complex compound was added to Calcein AM, the RFU (Relative Fluorescent Unit) value was low. However, it was confirmed that when the chelator (deferoxamine and vitamin C) continued to be added, the RFU value increased.

Example 2

Method for Detoxifying Ferrous-Salen Complex Compound, Using Deferasirox (Method)

Figure 2:
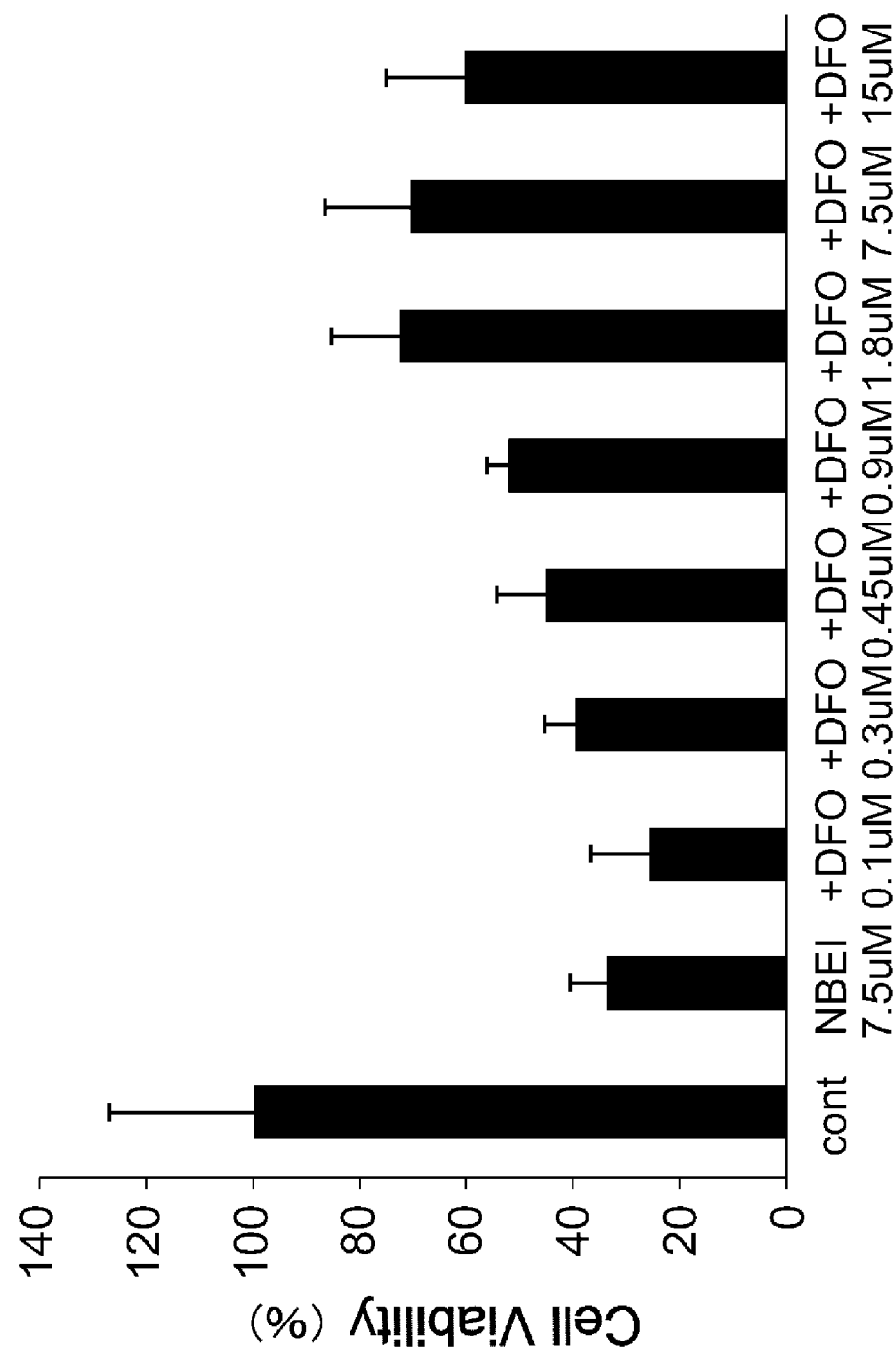
FIG. 2 is a graph showing measurement results of Example 2 (deferasirox [second metal chelating agent]) of the present invention.

POS-1 cells (mouse osteosarcoma cells) which are cancer cells were cultivated in 24-well plates (1.0×104/Well). After the cultivation for 24 hours, a 7.5 µM ferrous-salen complex compound (NBEI) was administered with a micropipette and deferasirox (DFO) was further administered by changing its concentration to 0.1 µM, 0.3 µM, 0.45 µM, 0.9 µM, 1.8 µM, 7.5 µM, and 15 µM, respectively. The cells were collected 24 hours later and an MTT reagent for cell survival assay was administered, 400 µL of 0.04-mol of HCl/isopropyl alcohol was added 45 minutes later, 100 µL of the obtained mixture was dispensed to 96-well plates, and absorbance at 570 nm was measured, thereby calculating cell viability. FIG. 2 shows the results.

(Results)

It was confirmed as illustrated in FIG. 2 that when the 7.5 µM ferrous-salen complex compound (NBEI) regarding which the cell viability of a control was 100% was added, the cell viability decreased. However, when the deferasirox was further added to the obtained mixture, the cell viability increased as the deferasirox concentration increased. In other words, the toxicity of the ferrous-salen complex compound was neutralized by the deferasirox. Incidentally, this effect did not change when the deferasirox concentration was 1.8 μM or more.

Method for Detoxifying Ferrous-Salen Complex Compound, Using Deferasirox and Vitamin C A 10 μM ferrous-salen complex compound (NBEI) was administered with a micropipette to cells cultivated in the same manner as in Example 2 above (after cultivation for 24 hours) and 7.5 μM deferasirox (DFO) and vitamin C were further administered by changing the concentration of vitamin C to 0.1 μM, 0.3 μM, 0.45 μM, 0.9 μM, 1.8 μM, 7.5 μM, and 15 μM, respectively. The cells were collected 24 hours later and the MTT reagent for cell survival assay was administered, 400 μL of 0.04-mol of HCl/isopropyl alcohol was added 45 minutes later, 100 μL of the obtained mixture was dispensed to 96-well plates, and absorbance at 570 nm was measured, thereby calculating cell viability. As a result, it was confirmed that the cell viability became higher than that of the control. In other words, it was confirmed that the toxicity of the ferrous-salen complex compound was neutralized by the deferasirox and vitamin C.

The invention claimed is:
1. A method for a treatment of cancer comprising:
    administering a magnetic Fe-salen complex compound to a body;
    externally applying a magnetic field to an affected site of the body and guiding the magnetic Fe-salen complex compound to the externally applied magnetic field site;
    administering a chelating agent to the body after suspending or terminating the externally applying the magnetic field; and
    neutralizing cytotoxicity of the magnetic Fe-salen complex compound, wherein the chelating agent absorbs Fe of the magnetic Fe-salen complex compound.
2. The method of claim 1, wherein the chelating agent is contained at 0.3 μM or more and 50 μM or less.
3. The method of claim 1, wherein the chelating agent is composed of the following compound:
    General Name: deferasirox

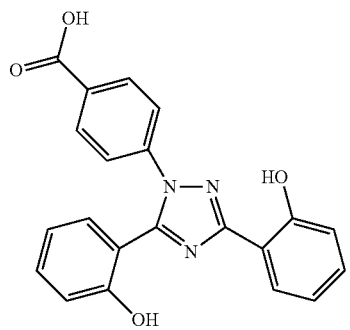 [SMILES: O=C(O)c1ccc(-n2nc(-c3ccccc3O)nc2-c2ccccc2O)cc1]

4. The method of claim 1, wherein the chelating agent is composed of the following compound:
    General Name: deferoxamine

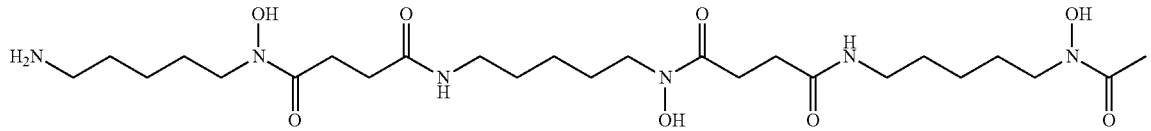 [SMILES: CC(=O)N(O)CCCCCNC(=O)CCC(=O)N(O)CCCCCNC(=O)CCC(=O)N(O)CCCCCN]

5. The method of claim 1, further comprising administering vitamin C to the body.

* * * * *